(12) United States Patent
Zhou et al.

(10) Patent No.: US 7,335,727 B2
(45) Date of Patent: Feb. 26, 2008

(54) PHARMACEUTICAL USED FOR TREATING HIV INFECTION, THE COMPOSITION AND USES THEREOF

(75) Inventors: Genfa Zhou, Tianjin (CN); Wangni Tian, Jilin (CN)

(73) Assignee: Tianjin Fusogen Biotech Co., Ltd., Tianjin (CN)

( * ) Notice: Subject to any disclaimer, the term of this patent is extended or adjusted under 35 U.S.C. 154(b) by 21 days.

(21) Appl. No.: 11/265,892

(22) Filed: Nov. 3, 2005

(65) Prior Publication Data
US 2006/0100139 A1  May 11, 2006

Related U.S. Application Data

(63) Continuation of application No. 10/487,724, filed as application No. PCT/CN02/00405 on Jun. 6, 2002, now Pat. No. 6,962,900.

(30) Foreign Application Priority Data
Aug. 29, 2001  (CN) ............................... 01 1 30985

(51) Int. Cl.
 *A61K 38/00* (2006.01)
(52) U.S. Cl. ................................... 530/325
(58) Field of Classification Search ................ None
 See application file for complete search history.

(56) References Cited

U.S. PATENT DOCUMENTS 6,962,900 B2 * 11/2005 Zhou et al. .................. 514/8

OTHER PUBLICATIONS

Tolerability of Enfuvirtide (T-20)during Chronic Therapy in Phase II Trials. Drobnes C, Fang L, Nelson E, True A, Salgo M, Delehanty J. Abstr Intersci Conf Antimicrob Agents Chemother Intersci Conf Antimicrob Agents Chemother. Sep. 27-30, 2002; 42: abstract No. H-171.*

Tremblay, C. L. et al "Strong in Vitro Synergy Between the Fusion Inhibitor T-20 and the CXCR4 Blocker AMD-3100" *JAIDS*, 2000, pp. 99-102, vol. 25.

Baba, M. et al. "Mechanism of Inhibitory Effect of Dextran Sulfate and Heparin on Replication of Human Immunodeficiency Virus In Vitro", *Proc. Natl. Acad. Sci. USA*, Aug. 1988, pp. 6132-6136, vol. 85.

Barré-Sinoussi, F. et al. "Isolation of a T-Lymphotropic Retrovirus from a Patient at Risk for Acquired Immune Deficiency Syndrome (AIDS)", *Science*, May 20, 1983, pp. 868-871, vol. 220.

Berger, E. A. et al. "Chemokine Receptors as HIV-1 Coreceptors: Roles in Viral Entry, Tropism, and Disease", *Annu. Rev. Immunol.*, 1999, pp. 657-700, vol. 17.

Bloom, B. R. "A Perspective on AIDS Vaccines", *Science*, Jun. 28, 1996, pp. 1888-1890, vol. 272.

Chan, D. C. et al. "Core Structure of gp41 from the HIV Envelope Glycoprotein", *Cell*, Apr. 18, 1997, pp. 263-273, vol. 89.

Clavel, F. et al. "Isolation of a New Human Retrovirus from West African Patients with AIDS", *Science*, Jul. 18, 1986, pp. 343-346, vol. 233.

Clercq, E. D. Novel Compounds in Preclinical/Early Clinical Development for the Treatment of HIV Infections, *Rev. Med. Virol.*, 2000, pp. 255-277, vol. 10.

Ferrer, M. et al. "Selection of gp41-Mediated HIV-1 Cell Entry Inhibiitors from Biased Combinatorial Libraries of Non-Natural Binding Elements", *Nature Structural Biology*, 1999, pp. 953-960, vol. 6, No. 10.

Gallo, R. C. et al. "Frequent Detection and Isolation of Cytopathic Retroviruses (HTLV-III) from Patients with AIDS and at Risk for AIDS", *Science*, May 4, 1984, pp. 500-503, vol. 224.

Gomatos, P. J. et al. "Relative Inefficiency of Soluble Recombinant CD4 for Inhibition of Infection by Monocyte-Tropic HIV in Monocytes and T Cells", *J. Immunology*, 1990, pp. 4183-4188, vol. 144, No. 11.

Jonassen, T. O. et al. "Sequence Analysis of HIV-1 Group O from Norwegian Patients Infected in the 1960s", *Virology*, 1997, pp. 43-47, vol. 231.

Jones, P. L. ST. J. et al. "Conformational Changes in Cell Surface HIV-1 Envelope Glycoproteins are Triggered by Cooperation Between Cell Surface CD4 and Co-receptors", *J. Bio. Chem.*, Jan. 2, 1998, pp. 404-409, vol. 273, No. 1.

Kilby, J. M. et al. "Potent Suppression of HIV-1 Replication in Humans by T-20, A Peptide Inhibitor of gp41-Mediated Virus Entry", *Nature Medicine*, Nov. 1998, pp. 1302-1307, vol. 4, No. 11.

Zsuzsanna, K-L. et al. "Pararetro- and retrovirus RNA: Splicing and the Control of Nuclear Export", *Trends in Microbiol.*, Dec. 1996, pp. 480-485, vol. 4, No. 12.

(Continued)

*Primary Examiner*—Cecilia J. Tsang
*Assistant Examiner*—Thomas S. Heard
(74) *Attorney, Agent, or Firm*—Saliwanchik, Lloyd & Saliwanchik

(57) ABSTRACT

A fusion inhibitor used to treat HIV infection, has an amino acid sequence as follows:

X-SWETWEREIENYTKQIYKI-
LEESQEQQDRNEKDLLE-Z, wherein X is either an amino group or -X1-X2, wherein X1 is an imino group, and X2 is either an acetyl group, a hydrophobic group, or a macromolecular carrier group; Z is a carboxyl group or -Z1-Z2, wherein Z1 is a carbonyl group, and Z2 is either an amino group, a tert-butyloxycarbonyl group, a hydrophobic group, or a macromolecular carrier group. This inhibitor has strong inhibitory activity against HIV infection.

10 Claims, 5 Drawing Sheets

OTHER PUBLICATIONS

Kliger, Y. et al. "Inhibition of HIV-1 Entry Before gp41 Folds Into its Fusion-active Conformation", *J. Mol. Biol.*, 2000, pp. 163-168, vol. 295.

Lenderkin, W. R. et al. "Evaluation of the Quality of Life Associated with Zidovudine Treatment in Asymptomatic Human Immunodeficiency Virus Infection" *N. Eng. J. Med.*, Mar. 17, 1994, pp. 738-743, vol. 330.

Maurer, K. et al. "Carbonyl J Derivatives: A New Class of HIV-1 Integrase Inhibitors", *Bioorganic Chemistry*, 2000, pp. 140-155, vol. 28.

McElrath, M. J. et al. "Human Immunodeficiency Virus Type 1 Infection Despite Prior Immunization with a Recombinant Envelope Vaccine Regiment", *Proc. Natl. Acad. Sci. USA*, Apr. 1996, pp. 3972-3977, vol. 93.

Pilcher, C. D. et al. "Prolonged Therapy with the Fusion Inhibitor T-20 in Combination with Oral Antiretroviral Agents in a HIV-infected Individual", *AIDS*, Oct. 22, 1999, p. 2171, vol. 13, No. 15.

Roe, T. et al. "3'-End Processing and Kinetics of 5'-End Joining during Retroviral Integration In Vivo", *J. Virology*, Feb. 1997, pp. 1334-1340, vol. 71, No. 2.

Weissenhorn, W. et al. "Atomic Structure of the Ectodomain from HIV-1 gp41", *Nature*, May 1997, pp. 426-430, vol. 387.

White, J. M. "Membrane Fusion" *Science*, Nov. 6, 1992, pp. 917924, vol. 258.

Wild, C. T. et al. "Peptides Corresponding to a Predictive α-helical Domain of Human Immunodeficiency Virus Type 1 gp41 are Potent Inhibitors of Virus Infection" *Proc. Natl. Acad. Sci. USA*, Oct. 1994, pp. 9770-9774, vol. 91.

Xiang, Y. et al. "Altered Rous Sarcoma Virus Gag Polyprotein Processing and Its Effects on Particle Formation", *J. Virol.*, Mar. 1997, pp. 2083-2091, vol. 71, No. 3.

Yu, E. S. H. et al. "HIV Infection and AIDS in China, 1985 through 1994", *Amer. J. Pub. Health*, Aug. 1996, pp. 1116-1122.

Zhou, G. et al. "The Structure of an HIV-1 Specific Cell Entry Inhibitor in Complex with theHIV-1 gp41 Trimeric Core", *Bio. Med. Chem.*, 2000, pp. 2219-2228, vol. 8.

Carpenter, C. J. C. et al. "Antiretroviral Therapy for HIV Infection in 1996" JAMA, Jul. 10, 1996, pp. 146-154, vol. 276, No. 2.

Condra, J. H. et al. "In Vivo Emergence of HIV-1 Variants Resistant to Multiple Protease Inhibitors" *Nature*, Apr. 6, 1995, pp. 569-571, vol. 374.

Dalgleish, A. et al. "The CD4 (T4) Antigen is an Essential Component of the Receptor for the AIDS Retrovirus", *Nature*, Dec. 1984, pp. 763-767, vol. 312.

Deeks, S. G. et al. "HIV-1 Protease Inhibitors: A Review for Clinicians", *JAMA*, Jan. 8, 1997, pp. 145-153, vol. 277, No. 2.

Fischl, M. A. et al. "The Efficacy of Azidothymidine (AZT) in the Treatment of Patients with AIDS and AIDS-Related Complex. A Double-Blind, Placebo-Controlled Trial" *N. Engl. J. Med.*, Jul. 23, 1987, pp. 185-191, vol. 317, No. 4.

Jiang, S. et al. "HIV-1 Inhibition by a Peptide" *Nature*, 1993, p. 113, vol. 365, No. 6442.

Lafeuillade A. et al. "Effects of a Combination of Zidovudine, Didanosine, and Lamivudine on Primary Human Immunodeficiency Virus Type 1 Infection", *J. Infect. Dis.*, 1997, pp. 1051-1055, vol. 175, No. 5.

Levy, J. A. (1988) Can an AIDS Vaccine be Developed? *Transfus. Med. Rev.* 2(4):264-271. (copies unavailable).

Levy, J. A. (2000) Acute HIV Infection and Susceptible Cells. 63-78. (copies unavailable).

Maddon, P. J. "The T4 Gene Encodes the AIDS Virus Receptor and is Expressed in the Immune System and the Brain", *Cell*, 1986, pp. 333-348, vol. 47, No. 3.

Miles, S. A. et al. "Protease Inhibitors", *International AIDS Society USA*, pp. 7-9, vol. 4, No. 3.

Myers, G. et al. "Evolutionary Potential of Complex Retroviruses", *The Retroviridae*, vol. 1, 1992, Jay A. Levy (ed.), Plenum Press, New York.

Vella, S. et al. "HIV Resistance to Antiretroviral Drugs" *International AIDS Society USA*, pp. 15-18, vol. 4, No. 3.

WHO Report 1996 (copies unavailable).

"AIDS Epidemic Update: Dec. 2000", WHO Report 2000, UNAIDS and WHO.

Burger et al. "Evolution of Human Immunodeficiency Virus Type 1 Nucleotide Sequence Diversity Among Close Contacts", *Proc. Natl. Acad. Sci. USA*, 1991, pp. 11236-11240, vol. 88.

* cited by examiner

Fig1 The amino acid sequence of Fusonex

As used herein, the single-letter codes represent amino acid residues.

1、 Fusonex) is a 36 amino-acid peptide.

SWETWEREIENYTKQIYKILEESQEQQDRNEKDLLE (SEQ ID NO.: 1)

2、 HIV-1 (E subtype) gp41 C peptide (117-151).

WIEWEREISNYTNQIYEILTESQNQQDRNEKDLLE (SEQ ID NO.: 2)

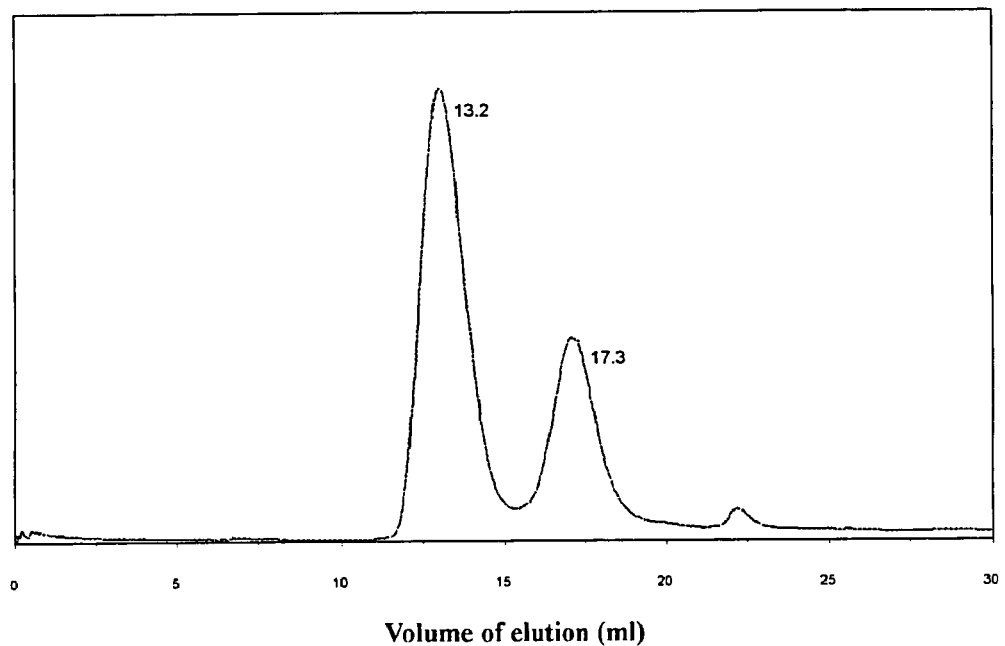
Fig 2. Elution profile on Superdex-75 column

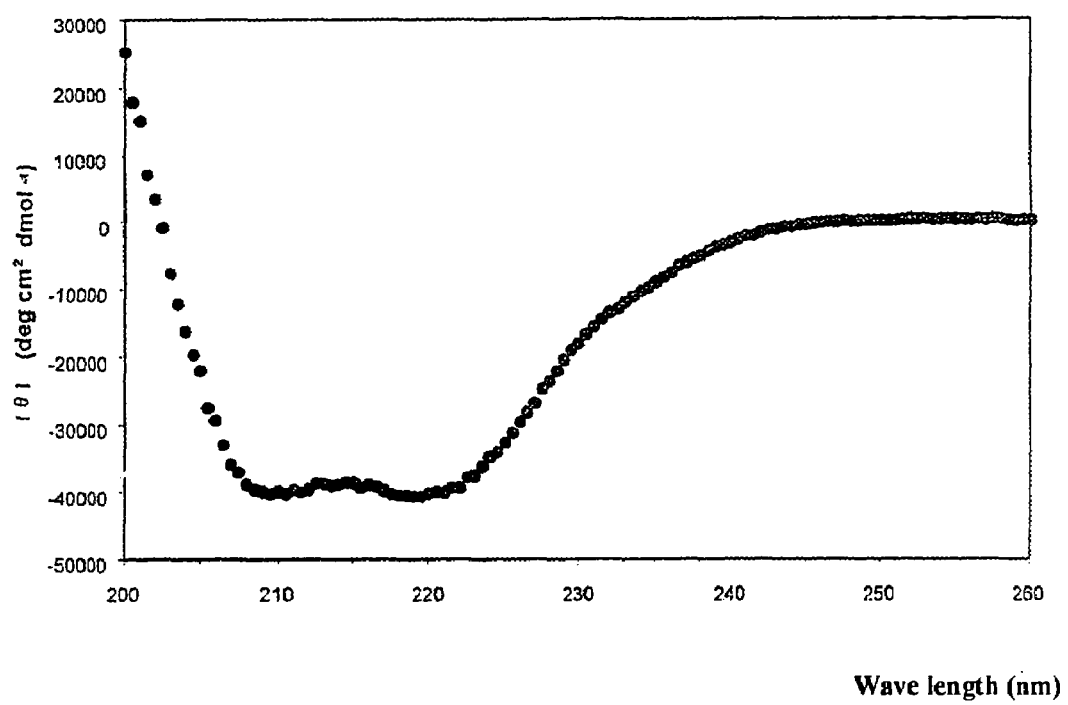
Fig3 Circular dichroism (CD) spectrum

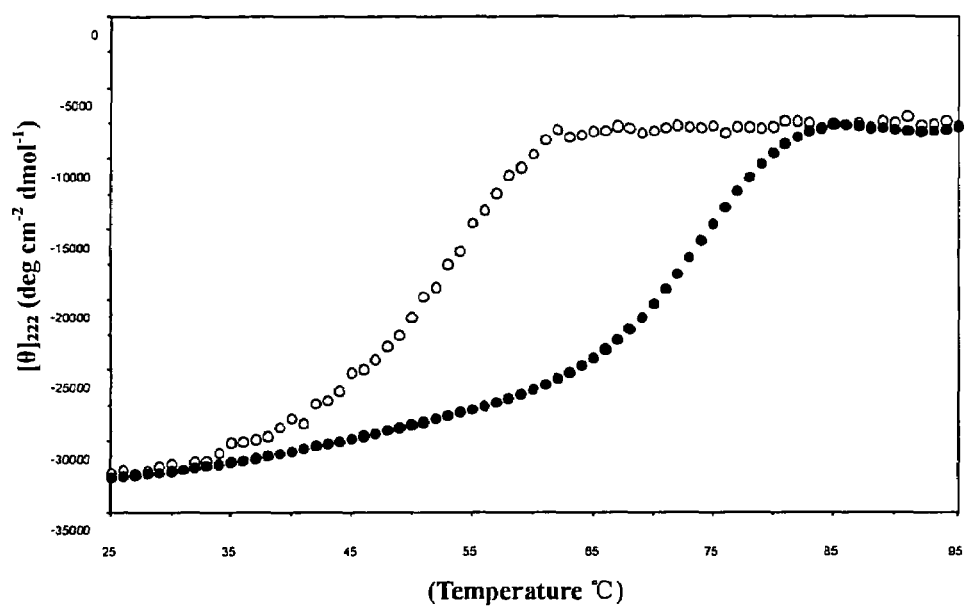

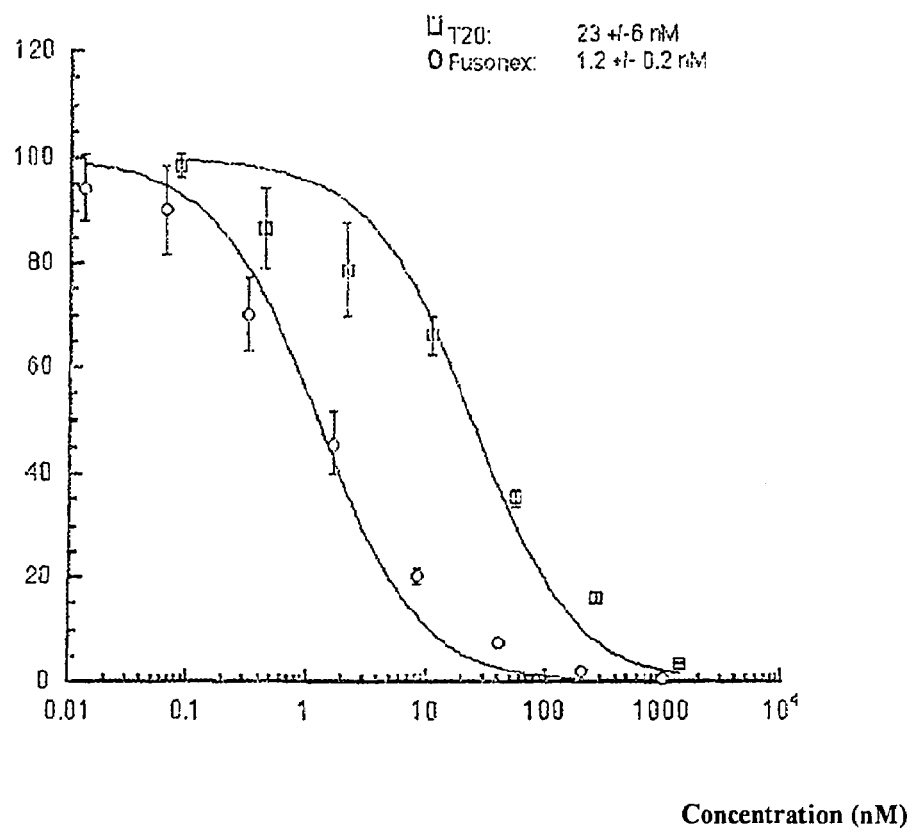
Fig5 The inhibition profiles of Fusonex and T-20 against viral fusio

PHARMACEUTICAL USED FOR TREATING HIV INFECTION, THE COMPOSITION AND USES THEREOF

CROSS-REFERENCE TO RELATED APPLICATIONS

This application is a continuation of U.S. Ser. No. 10/487,724, filed Jul. 19, 2004; now U.S. Pat. No. 6,962,900 which is the National Stage filing of International Application No. PCT/CN02/00405, filed Jun. 6, 2002; which claims priority to Chinese Patent Application No. 01130985.7, filed Aug. 29, 2001, now Chinese Patent No. ZL 01130985.7, all of which are incorporated herein by reference in their entirety.

FIELD OF TECHNOLOGY

The present invention relates to a fusion inhibitor, which can be used in the treatment of HIV infection.

BACKGROUND OF THE INVENTION

1. HIV and AIDS Epidemic

Infection with Human Immunodeficiency Virus (HIV), a pathogenic retrovirus, can cause Acquired Immunodeficiency Syndrome (AIDS) (Barre-Sinossi, F. et al., 1983, *Science* 220: 868-870). Although macrophage, neuron and other cells can be infected by HIV (Maddon et al., 1986, *Cell* 47:333-48) the CD4+ lymphocytes are the major target cells for HIV (Dalgleish, A. et al., 1984, *Nature* 312:767-8), because HIV has strong affinity to the CD4 molecules on the surfaces of CD4+ cells. HIV infection in a human body destroys so many CD4+ lymphocytes that the body begins to lose its immune function, therefore an AIDS patient is highly vulnerable to various infections, neuronal dysfunction, tumors, and so on. Suffering from the symptoms, the patients die eventually (edited by Levy, J. A.: Acute HIV infection and susceptible cells, published in U.S.A, 2000, Page 63-78)

With its severe symptoms and high mortality rate, the epidemic contagion of AIDS has become one of the leading causes of death that is threatening human health. So far in the entire world, people infected by HIV have accumulated to a total of 57,900,000. 21,800,000 people have died from AIDS in the last decade. 5,300,000 people were found to have newly contracted HIV within the year 2000. In China, HIV infection spreads rapidly. Experts estimated that in 2000 the population of HIV positives has exceeded 800,000-1,000,000, which includes both adults and children (WHO Report 2000, UNAIDS and WHO).

Currently at least two types of HIV have been identified: HIV-1 (Gallo, R. et. al., 1984, *Science* 224:500-503) and HIV-2 (Clavel, F. et al., 1986, *Science* 223:343-346). Each of them has high genetic heterogeneity. For HIV-1 alone, there are at least 11 different genotype (A-J and O subtypes) (Jonassen, T. O. et al., 1997, *Virol.* 231:43-47). The E subtype of HIV-1 is distributed mainly in Central Africa, Thailand, India, Vietnam, Kampuchea, Malaysia, Burma, China, and western hemisphere (WHO Report 1996). The HIV subtypes found in China are mostly B, E, or C subtype (Yu, E. S. et al., 1996, *American J. Public Health* 86(8 Pt1): 1116-22).

The reproduction cycle of HIV has several important steps. First, the envelope glycoprotein gp120 attaches itself to the host cell membrane through its specific binding with CD4 molecule located on the surface of T4 lymphocyte. With the assistance of chemokine co-receptor, the viral envelope fuses with the host cellular membrane (Berger, E. A., et al., 1999, *Ann. Rev. Immunol,* 17: 657-700). After the fusion process, the HIV virion packed in nucleocapsid enters into the host cell with its capsid shucked off and viral nucleic acid exposed. The viral reverse transcriptase catalyzed the transcription of HIV single-stranded RNA into single-stranded DNA, which is then transformed to double-stranded DNA by the catalysis of cellular polymerase. The double-stranded DNA can either exist freely in cytoplasm or be integrated as provirus into host chromosome DNA by the catalysis of viral integrase, thus engendering HIV latent infection (Roe, T. et al., 1997, *J. Virol.* 71(2):1334-40). Provirus, which will not be excised from the host chromosome, is very stable and reproduces itself with the replication of host chromosome. After the HIV mRNA is translated into a large polyprotein, the viral proteases cut and process the polyprotein to form mature viral structural proteins (Xiang, Y. & Leis, J., 1997, *J. Virol.* 71(3): 2083-91). These structural proteins, together with HIV nucleic acids, are finally assembled into new virus granules and released outside the cell by budding (Kiss-Lazozlo, Hohn, T., 1996, *Trends in Microbiology* 4(12):480-5).

In summary, the critical stages of HIV replication are: 1) attachment and entry into host cell through a fusion process; 2) reverse transcription and integration; 3) protein translation and processing; 4) virus assembly and release.

2. The Treatment for HIV Infection

Although great efforts have been dedicated to effective remedial and preventive methods for many years, there is no working vaccine or cure for AIDS yet.

An ideal vaccine should be innocuous and capable of inducing neutralizing antibodies as well as persistent immune responses in mucous membrane and blood (Levy, J. A. and Levy, J. A., 1988, *Trens Med. Rev.* 2:265-71). Many HIV vaccines currently developed in the world are still in the stages of animal trials. Although vaccines against HIV membrane proteins gp160 and gp120 have already moved into first, second, or third stages of clinical trials, the results of the trials are disappointing. Many vaccines that are effective to prevent HIV infection in laboratory animals are not effective in human (McElrath, M. J. et al., 1996, *Pro. Natl. Acad. Sci. USA* 93:3972-77). The fact that scientists are making little progress in HIV vaccine research could be attributed to the complexity and variability of HIV genetic materials (Bloom, B. R., 1996, *Science* 272:1888-1900).

The drugs against AIDS approved in the world could be classified into two categories: HIV reverse transcriptase inhibitors (Charles, C. J., et al., 1996, *JAMA* 276:146) and HIV protease inhibitors (Miles, S. A. et al., *International AIDS Society USA* 4(3): 15). Both of them aim at later stages of HIV infection—transcription and assembly of new viruses. The well-known "Cocktail Therapy" is a combination therapy using both types of inhibitors (Lafeuillade, A., et al., 1997, *J. Infect. Dis.* 175:1051-55).

Reverse transcriptase inhibitors, including AZT, ddI, ddC, 3TC, and d4T, etc, would induce drug resistance, sooner or later, that means the viruses become less sensitive to the drugs, and the effective inhibition concentration of the drugs rise by several-fold or even ten-fold (Vella, S. and Floridia, M., 1996, *International AIDS Society USA* 4 (3):15) This drug-resistance is associated with high mutation rate of HIV. In a human body, a single HIV virus could produce $10^8$-$10^{10}$ new virus granules every day, while the mutation rate is $3 \times 10^5$ per replication cycle. Many mis-sense mutations, affecting the expression of amino acids, may happen in the regulatory genes as well as in the envelope proteins. In some HIV strains, the mutation rate could be as high as 40% in the amino acid sequences of certain genes (Myers, G and Montaner, J. G., 1992, The Retroviridae vol. 1, Plenum Press, New York 51-105). As a result, reverse transcriptase inhibitors lead to drug-resistance by facilitating the proliferation of resistant strains that exist before and after the mutations in addition to control sensitive virus strains.

Moreover, all the reverse transcriptase inhibitors have specific toxicity related to their dosage. The symptoms include spinal cord suppression, vomiting, liver dysfunction, muscle weakness, diseases of peripheral nervous system, and pancreatic inflammation. Many patients have to suspend the treatment due to these intolerable side effects (Fischl, M. A., et al., 1987, *N. Engl. J. Med.* 317:185-91; Lenderking, W. R., et al., 1994, *N. Engl. J. Med.* 330:738-43).

Drug-resistance is also a major problem for protease inhibitors. Mutations in viral protease gene have caused drug-resistance in all the protease inhibitors presently used in AIDS treatment (Condra, J. H. et al., 1995, *Nature* 374:569-71). The side effects of protease inhibitors include liver dysfunction, gastrointestinal discomfort, kidney stone, numbness around mouth, abnormality of lipid metabolism, and mental disorder (Deeks, et al., 1997, *JAMA* 277:145-53).

In summary, most of the currently used anti-HIV drugs are highly toxic, and induce drug-resistance. Therefore, there is still a huge obstacle in the treatment of HIV infection. Apparently, it is urgent for the need of new drugs with better efficacy and lower toxicity for the treatment of HIV infection.

New drugs can be developed against new targets in different stages of HIV replication cycle. Recently a few of anti-AIDS drugs with new mechanisms have been developed after in-depth research in HIV and AIDS. These drugs include some new HIV reverse transcriptase inhibitors and HIV protease inhibitors, as well as some new anti-HIV agents aimed at other targets that are listed here (De, C. E., 2000, *Rev. Med. Virol.* 10 (4):255-77):

1). Virus absorbents, such as sodium lauryl sulfate, dextrose sulfate, and heparin, can interrupt the cohesion of gp120 on HIV envelope and the lymphocyte through the action of polyanion groups. However, these absorbents have bad specificity and high toxicity. Some of them can even increase the virus load (Baba, M., et al., 1988, *Pro. Natl. Acad. Sci. USA.* 85:6132-6);

2). Soluble CD4s are used to prevent gp120 from binding to host cells. Some recombinant soluble CD4s could bind the virus granules before gp120 contact the CD4 molecules on cellular membrane and prevent HIV infection. However, these recombinant soluble CD4s are of no apparent effect on the HIV-1 strains isolated from some patients. Moreover, the clinical experiments did not provide any reliable evidence for their antiviral activity (Gomatos, P. J. et al., 1990, *J. Immunol.* 144:4183-8);

3). Chemokines and their analogs, including RANTES, MIP-1α, MIP-1β binding with CCR5 and SDF binding with CXCR4, can be used to prevent HIV from entering into host cells. They could not only competitively block the gomphosis between HIV gp120 and cellular chemokine co-receptors but also limit HIV inbreak points by depressing the expression of this co-receptor on cell. The latest chemokine co-receptor blockers include positive charged small peptides such as ALX40-4C and T22, and compounds such as AMD3100, TAK-779 and trichosanthin.

4). Although soluble CD4-IgG can suppress HIV replication in vitro, it has no reliable antiviral activity in clinical trials.

5). Agents such as 2,2'-dithiobisbenzamides (DIBAs) and azadicarbonamide (ADA) can block the assembly and disassembly of viruses through interactions with NCp7 zinc finger site.

6). A segment of gp41 or its analog can be used as a fusion inhibitor. For example, T-20 is capable of blocking virus entry into the cell (Jiang, S. et al., 1993, *Nature* 365:113.)

7). Inhibitors of viral mRNA transcriptase, such as CGP64222, fluoroquinolone K-12, and EM2487;

8. Inhibitors of integrase, such as derivatives of Carbonyl J [N,N'-bis(2-(5-hydroxy-7-naphthalenesulfonic acid)urea], can prevent HIV from integrating its genome into host lymphocyte genome (MaurerK, et al: 2000, *Bioorg Chem* 28(3):140-155)

3. Fusion Inhibitors Blocking Viral Entry into Cells

Many biological processes involve membrane fusion. In eukaryotic cells, the fusions of cellular membranes are happening continuously, including endocytosis, secretion, recycle of membranous components, and so on (White, J. M., 1992, *Science* 258:917-24). Examples of fusion in some peculiar cells include the secretion of regulated fusion hormone, enzyme, and nerve transmitter. Some more notable examples include the fusion of germ cells and of muscle cells.

According to an embodiment of the present invention, the anti-fusion or anti-membrane fusion drug is an agent that inhibits or suppresses the fusion of two or more biological membranes. According to an embodiment of the present invention, two or more biological membranes are either cellular or viral structures, such as cellular membrane and viral envelope. According to an embodiment of the present invention, the antiviral agent is a compound that inhibits viral infection of cells, such as the inhibition of virus-cell fusion, or cell-cell fusion. According to an embodiment of the present invention, the infection is related to membrane fusion, such as envelope viral infection of cells, and other processes similar to viral and cellular fusion, such as what happens during bacterial conjugation.

In conclusion, membrane fusion is a critical step for envelope virus to attack and penetrate the host cells (Weissenhorn, W., et al., 1997, *Nature* 387:426-30). The anti-HIV drug of the present invention, Fusonex, as well as its derivatives, is a fusion blocker to prevent viruses from entering host cells.

The fusion process is controlled by the glycoproteins on HIV envelope. The precursor of the glycoproteins is gp160 that has polysaccharide groups. During the virus reproduction period, gp160 is hydrolyzed by certain protease into two subunits: gp120, which is outside the envelope, and gp41, which is a trans-membrane protein. After the hydrolyzation, gp120 and gp41 are still linked by non-covalent bonds and polymerized as trimers outside the virus granule. The trans-membrane protein gp41, whose ectodomain with a highly helical structure, has a highly efficient origination mechanism for membrane fusion, and is known as the pivotal molecule to open the gate of cells for its direct participation in the fusing process of cellular membranes (Ferrer, M., et al., 1999, *Nat. Struct. Biol.* 6(10):953-60; Zhou, G, et al., 2000, 1:*Bioorg. Med. Chem.* 8(9):2219-27).

It has been demonstrated by crystal diffraction analysis that when fusion takes place between viruses and cells, the core of gp41 is composed of six helical bundles wherein the N-terminal and C-terminal helices are collocated as three hairpins which fix the HIV envelope to the cellular membrane. While the gp41 trimer can form a fusion pore that facilitates the viral intrusion into the host cell (Chan, D. C., et al., 1997, *Cell* 89:263-73), it exists in an unstable natural non-fusion conformation on the surface of the free virus granule fresh sprouting from infected cells. At first, the N-terminal helix is wrapped inside the C-terminal helix so that the N-terminal fusion area is hidden, then after gp120 on viral surface combines with the CD4 receptor and chemokine co-receptor on the cellular membrane, an receptor-activated conformational change of gp41 occurs in which its N-terminal extends beyond the viral surface into the host cellular membrane. At this time, gp41 is transformed from an unstable natural non-fusion conformation into a pro—hairpin intermediate conformation. When the C-terminal and N-peptides of gp41 bind together, the hydrophobic N-terminal core of the trimer structure is exposed, and the pro-hairpin intermediate is transformed into a more energy-stabilized hairpin conformation, and by this time the viral envelope has fused with the cellular membrane (Jones, P. L., et al., 1998, *J. Biol. Chem.* 273:404).

The first fusion inhibitor ever discovered is a 36 amino-acid peptide derived from the C-terminal (127-162) of gp41-T-20, its sequence is as follows:

X-YTSLIHSLIEESQNQQEKNEQELLELK-WASLWNWF-Z.

The structural similarity of T-20 to the C-terminal of gp41 makes it capable of competing with the C-peptide of gp41 in binding with its N-terminal fusion area. On the surface of T-cell, T-20 at very low concentration can interrupt the fusion between HIV gp41 and host cellular membrane (the $IC_{50}$ is within the range of nM) (Jiang, S., et al., 1993, *Nature* 365:113; Wild, C. T. et al., 1994, *Pro. Natl. Acad. Sci. USA* 91:9770-74). In the pro-hairpin state which lasts many minutes, T-20 is very effective in inhibiting the binding of the C-peptide of gp41 with its N-terminal fusion area, thus blocking the formation of a hairpin between the viral envelope and cellular membrane (Kliger, Y and Shai, Y, 2000, *J. Mol. Biol.* 295:163-8).

Because a fusion inhibitor acts on the cellular membrane, it doesn't need to be released inside cells to exert its function. In comparison, the anti-HIV drugs, currently in clinical use, all act in the middle or late stages of viral infection of host cells, that means they must be first released into the cells to be able to inhibit the reproduction of the invading HIV. In addition, the highly conserved amino acid sequence of the hydrophobic core of gp41 suggests that the virus is not likely to develop drug resistance against the fusion inhibitors. It is shown in vitro experiments that T-20 can specifically block HIV entry into cells. On the other hand, both the first and the second stages of clinical trials have indicated that AIDS patients can put up well with T-20 administration. T-20 has no toxicity against the spinal cord, and the most side effects are in low grade, or in middle grade. In a daily dosage of 200 mg, T-20 can remarkably reduce the HIV loads in most patients, and 30% has fallen below a detectable level (lower than 400/ml). Besides, T-20 is also effective to HIV patients who have already developed drug resistance. It is reported that the number of CD4+ cells in some patients has undergone some increase after the use of T-20 (Kilby, J. M. et al., 1998, *Nat. Med.* 4:1302-1307). It has been worried that long term administration of T-20 might induce the production of specific antibodies against T-20, that could cause the AIDS patients resistance to T-20. Nevertheless, during an experiment of a few weeks, T-20 maintained antiviral activity all the time (Pilcher, C. D. et al., 1999,*AIDS* 13(15):2171-4).

Compared with the HIV reverse transcriptase inhibitors and protease inhibitors currently in clinical use, the advantages of the fusion inhibitor T-20 are better efficacy, lower toxicity, and no drug resistance yet. However, the clinical dosage of T-20 is as high as 200 mg per day is an indication of its bad stability and low anti-fusion valence. In addition, because of such high dosage, T-20 has caused some local responses in some patients (Kilby, J. M. et al., 1998, *Nat. Med.* 4:1302-1307)

SUMMARY OF THE INVENTION

The present invention provides fusion inhibitors with both high stability and high valence for the treatment of HIV infection. The fusion inhibitors of the present invention can be used in combination therapies against AIDS, in production methods, or in other applications. In comparison with T20, The inhibitors of the present invention have higher efficacy, and lower administration dosage, and thereby lower toxicity.

According to an embodiment of the present invention, the fusion inhibitor is a specific peptide of 36 amino acid residues, with terminal-capping groups added to both ends of the peptide.

The present invention provides the following technology schemes:

According to a preferred embodiment of the present invention, the fusion inhibitor is a peptide derived from HIV trans-membrane glycoprotein gp41. According to a further preferred embodiment of the present invention, the peptide has an amino acid sequence as set forth in SEQ ID NO.: 1, and is set forth as follows:

(SEQ ID NO.: 1)
X-SWETWEREIENYTKQIYKILEESQEQQDRNEKDLLE-Z.

In the peptide (It is also called Fusonex in the following description),

X is an amino group or -X1-X2, wherein X1 is an imino group, and X2 is an acetyl group, a hydrophobic group, or a macromolecule vector group; the hydrophobic group is preferably an acarbobenzoxy group, a dansyl group, a tert-butyloxycarbonyl group, or a 9-fluorenylmethyloxycarbonyl group; the macromolecule vector group is a lipid-fatty acid chelate, a polyethylene glycol, or a carbohydrate;

Z is a carboxyl group or -Z1-Z2, wherein Z1 is a carbonyl group, and Z2 is an amino group, a tert-butyloxycarbonyl group, a hydrophobic group, or a macromolecule vector group.

As used herein, the single-letter codes representing amino acid residues are defined as follows:
A Alanine
R Arginine
N Asparagines
D Aspartic acid
C Cysteine
Q Glutamine
E Glutamic acid
G Glycine
H Histidine
I Isoleucine
L Leucine
K Lysine
M Methionine
F Phenylalanine
P Proline
S Serine
T Threonine W Tryptophan
Y Tyrosine
V Valine According to a preferred embodiment of the present invention, X2 or Z2 or both are hydrophobic group. The hydrophobic group is an acarbobenzoxy group, a dansyl group, a tert-butyloxycarbonyl group, or a 9-fluorenylmethyloxycarbonyl group.

According to an alternative embodiment of the present invention, X2 or Z2 or both are macromolecule vector group. The macromolecule vector group is a lipid-fatty acid chelate, a polyethylene glycol, or a carbohydrate.

In a further preferred embodiment of the present invention, the above-mentioned X2 is an acetyl group, and Z2 is an amino group.

According to an embodiment of the present invention, a composition for combination therapy against AIDS comprises the inhibitor, and at least one component selected from the group consisting of reverse transcriptase inhibitors, virus protease inhibitors, glycosidase inhibitors, viral mRNA capping inhibitors, amphotericin B, ester bond binding molecules castanospermine with anti-HIV activity, hydroxyurea, α-interferon, β-interferon, and γ-interferon.

According to a preferred embodiment of the present invention, the reverse transcriptase inhibitor is at least one selected from the group consisting of AZT (3'-azide-2',3'-dideoxycytidine), ddI (2',3'-dideoxyinosine), ddC (2',3'-dideoxycytidine), ddA (2',3'-dideoxyadenosine), d4T (2',3'-dideoxy-dideoxythymidine), 3TC, Nevirapine, Atevirapine, Delavirdine, PMEA, PMPA, and/or loviride; the glycosidase inhibitor is SC-48334 or MDL-28574 or both; the viral mRNA capping inhibitor is ribovirin.

The present invention also provides the inhibitor to be administered for the treatment of HIV infection via injection, in oral dosage formulation, in rectal dosage formulation, or in percutaneous dosage formulation;

A composition containing the inhibitor can also be administered for the treatment of HIV infection via injection, in oral dosage formulation, in rectal dosage formulation, or in percutaneous dosage formulation.

The inhibitor can be manufactured by applying common techniques and methods known in the field. For instance, small peptides can be synthesized on a certain vector or in a solution. Longer peptides can be produced by recombinant DNA technology, or can be synthesized as several distinct segments and then connected together. The nucleotide sequence encoding the peptide can be synthesized and/or cloned and expressed through the technology familiar to an ordinary technician in this field.

One or more of the peptide bonds of the inhibitor connecting amino acid residues can be replaced by non-peptide bonds including (but not limited to) imino, ester, phthalhydrazide, semicarbazide, azo bonds, etc. The non-peptide-bond replacement reactions are common knowledge to one of skill in the art. This peptide can also be synthesized by putting other chemical groups to its amino and/or carboxyl terminal to enhance its stability, bioavailability, and/or inhibitory activity, etc. For example, hydrophobic groups, such as carbobenzoxy, dansyl, or tert-butyloxycarbonyl group, can be added to the amino terminal, and acetyl or 9-fluorenylmethyloxycarbonyl can also be placed at the amino terminal. The above-mentioned hydrophobic group, tert-butyloxycarbonyl group, or amino group can be added to the carboxyl terminal of the peptide. In addition, the peptide can be synthesized by changing its spatial conformation. For instance, one or more amino acids of the peptide can use their D-isomers instead of the usual L-isomers.

Besides, at least one amino acid residue of the present inventional peptide can be replaced by a known non-natural amino acid residue in order to enhance its stability, bioavailability, and/or fusion inhibitory activity.

Furthermore, any of the above-mentioned peptides can have a non-peptide macromolecular vector group linked to their amino and/or carboxyl terminal through a covalent bond, including (but not limited to) a lipid-fatty acid chelate, a polyethylene glycol, or a carbohydrate.

BRIEF DESCRIPTION OF THE DRAWINGS

FIG. 1 shows the amino acid sequence of Fusonex (SEQ ID NO.: 1), which is a polypeptide composed of 36 amino acids. Fusonex is derived from the amino acid sequence (117-151) (SEQ ID NO.: 2) at the C-peptide of HIV-1 gp41 (E subtype). In all the figures, the above-mentioned single-letter codes are used for amino acids.

FIG. 2 is the elution profile showing the characteristic peaks of Fusonex and the complex of Fusonex and gp41 N-peptide (35-70) from Superdex chromatography column.

FIG. 3 is the circular dichroism spectra of the macromolecular secondary structure of the complex of Fusonex and gp41 N-peptide (35-70).

FIG. 4 shows the stability comparison between Fusonex and T-20, wherein the curve on the right side (solid circle) is the melting curve of Fusonex complexed with gp41 N-peptide, and the curve on the left side (hollow circle) is the melting curve of T-20 complexed with gp41 N-peptide. It had been shown that, in the range of 35-80° C., Fusonex is more stable than T-20 at the same temperature.

FIG. 5 shows the fusion inhibitory activities of Fusonex and T-20. In this experiment, the activity of luciferase was used for quantitative analysis of the fusion inhibitory activities of Fusonex (circle) and T-20 (square). The cellular fusion was induced by HIV-1 gp160$_{HXB}$. When the effector cell expressing gp160$_{HXB}$ gene and T7 polymerase gene fuses with the target cell expressing CD4 gene and luciferase reporter gene, the luciferase gene is expressed and a chemical fluorescence is radiated. This experiment defines as 100% the luciferase activity of the control group in the absence of any fusion inhibitor. It had been shown that, at the same concentration, Fusonex has a better inhibiting activity than T-20, based on the comparison of their inhibition activities of the cell fusion induced by HIV-1 gp160$_{HXB}$.

DETAILED DESCRIPTION OF THE INVENTION

Based on the analysis of the three-dimensional structure of gp41, the present invention provides a novel fusion inhibitor—Fusonex. Detailed descriptions of the antiviral peptide involved in the present invention are listed as follows:

1. Fusonex is a polypeptide composed of 36 amino acid residues. Fusonex (SEQ ID NO.: 1) is derived from the segment (the amino acid sequence from No. 117 to No. 151) (SEQ ID NO.: 2) of the C peptide of the ectodomain of HIV-1 (Subtype E) trans-membrane protein gp41, its amino acid sequence of this segment is as follows:

(SEQ ID NO.: 2)
WIEWEREI SNYTNQIYEILTESQNQQDRNEKDLLE

2. Add S (serine) to the N-terminal, because serine is generally added to the N-terminal of a α-helix to increase its stability.

3. Substitute E (Glutamic acid) for I (Isoleucine) at No. 118, so that it forms a charge-charge interaction with R (Arginine) at No. 122, which can increase the stability of the α-helix.

4. Substitute T (Threonine) for E (Glutamic acid) at No. 119, the intention is to cover the hydrophobic pocket including W(Tryptophan)117, W120 and W60.

5. Substitute E (Glutamic acid) for S (Serine) at No. 125, so that it can form a charge-charge interaction with K (Lysine) at No. 129, which can increase the stability of the α-helix.

6. Substitute K (Lysine) for N (Asparagines) at No. 129, so that it can form a charge-charge interaction with E (Glutamic acid) at No. 125, it can increase the stability of the α-helix.

7. Substitute K (Lysine) for E (Glutamic acid) at No. 133, so that it can form a charge-charge interaction with E (Glutamic acid) at No. 136 and No. 137, it can increase the stability of the α-helix.

8. Substitute E (Glutamic acid) for T (Threonine) at No. 136, so that it can form a charge-charge interaction with K (Lysine) at No. 133, it can increase the stability of the α-helix.

9. Substitute E (Glutamic acid) for N (Asparagines) at No. 140, so that it can form a charge-charge interaction with R (Arginine) at No. 144, it can increase the stability of the α-helix.

After a series of the above-mentioned alterations, the new viral fusion inhibitor Fusonex is composed of the following amino acid sequence:

```
                                         (SEQ ID NO.: 1)
    SWETWEREIENYTKQIYKILEESQEQQDRNEKDLLE
```

The present invention provides a peptide (Fusonex) with high-valence antiviral activity. Fusonex has 36 amino acids and is derived from the C-terminal amino acid sequence (No. 117-151) of the ectodomain of HIV-1 (subtype E) trans-membrane glycoprotein gp41. The polypeptide Fusonex in the present invention, even at very low concentration, is capable of blocking the fusion process between viruses and cells, and between virus-infected cells and uninfected ones. By blocking the entry, Fusonex is capable of preventing the viruses from entry into cells, as well as containing the spreading of viruses from infected cells to uninfected ones.

According to the virus-cell fusion assay, the fusion inhibition concentration for Fusonex is 20-fold lower than that of T-20. Thus, the peptide of the present invention has an improved efficacy in fighting against HIV infection, and should have a reduced toxicity. Thanks to its high stability and high efficacy, the peptide of the present invention is a much better inhibitor against virus fusion than T-20.

The antiviral activity of Fusonex includes (but not limited to) preventing HIV from spreading to uninfected CD4+ cells and other cells. In addition, the antiviral activity of the inhibitor of the present invention does not require the elicitation of any immune response in the host.

The inhibitor of the present invention can be applied to any biological fields related to membrane fusion inhibition, including prevention of the transmittal of human or non-human retrovirus (especially HIV) from uninfected cells. According to a preferred embodiment of the present invention, the inhibitor Fusonex and its derivatives are used as inhibitors of retrovirus (especially HIV) transmittal to uninfected human or non-human cells.

The inhibitor of the present invention can also regulate those biological processes inside the cells that are related to the secondary structure of coiled protein helices. As used herein, "Regulate" refers to an activating or a suppressing effect by the peptide of the present invention on the level or the extent of a certain biological activity inside the cells (compared to the situation in the absence of the peptide in the present invention).

The inhibitor of the present invention can also be used to identify compounds with inhibitory activity of virus fusion, antiviral compounds, and compounds with regulative activities inside the cell. In addition, the Fusonex in the present invention can also be applied to the diagnosis of a specific biological, viral types, and/or viral subtypes.

The present invention provides a novel fusion inhibitor, Fusonex, and its derivatives. The present invention also provides a joint administration of Fusonex or its derivatives with other agents, such as other antiviral agents, in the treatment and/or prevention of viral infection, especially HIV infection. These agents may or may not have the same sites or mechanisms in action as viral fusion inhibitors. As a result, cooperative or synergistic effects may result from joint drug administration.

According to an embodiment of the present invention, Fusonex or its derivatives can be administered with other agents in all the following, including (but not limited to): simultaneous administration, sequential administration, periodic administration, and periodic therapy (for example, administration of an antiviral compound, then a second antiviral compound within a certain period of time, repeating such administration sequence (namely the period) to reduce possible drug resistance of the antiviral therapy).

The combination therapy of Fusonex or its derivatives with other antiviral agents provides a novel therapeutic method that can reduce the effective dose and thus the toxicity of these antiviral therapies. Furthermore, drug combination can inhibit viral infection of host cells through different mechanisms, which not only increase the antiviral efficacy but also prevent the viruses from building up tolerance against any therapy alone. The probability of successful therapy is therefore increased.

The present invention also provides drug combination and preparations as therapies or as preventives of virus (especially HIV) infection. This drug combination comprises Fusonex or its derivatives in effective dose, at least one of other agents, and/or a pharmacologically acceptable vector.

The agents used jointly with Fusonex or its derivatives include any drugs which are known or under experiment. According to a preferred embodiment of the present invention, Fusonex or its derivatives are administered together with another agent with a different mechanism. These agents include (but not limited to): antiviral agents, such as the cytokines rIFNα, rIFNβ, and rIFNγ, reverse transcriptase inhibitors, such as AZT, 3TC, ddI, ddC, Nevirapine, Atevirapine, Delavirdine, PMEA, PMPA, Loviride, and other dideoxyribonucleosides or fluorodideoxyribonucleoside; viral protease inhibitors, such as Saquinarir, Ritonavir, Indinavir, Nelfinavir, and VX-478; hydroxyurea; viral mRNA capping inhibitors, such as viral ribovirin; amphotericin B; ester bond binding molecule castanospermine with anti-HIV activity; glycoprotein processing inhibitor; glycosidase inhibitors SC-48334 and MDL-28574; virus absorbent; CD4 receptor blocker; chemokine co-receptor inhibitor; neutralizing antibody; integrase inhibitors, and other fusion inhibitors.

Therefore, the present invention provides an improved antiviral therapy for the treatment of broad viral (including HIV) infection. In addition, the present invention provides a method of joint drug administration aimed at boosting the therapeutic effect, including the use of Fusonex, its derivatives, at least a different medicine, and/or a pharmacologically acceptable vector. The combination therapy can prevent the virus from building up a tolerance against each therapeutic alone, and at the same time reduce drug toxicity and enhance the therapeutic index.

As used herein, "viral infection" refers to a morbid state in which the virus invades a cell. When the virus enters the healthy cell, it takes advantage of the host reproduction mechanism to reproduce itself, then finally kills the cell. After budding from the cell, those newly produced progeny viruses go on to infect other cells. Some viral genes can also integrate into host chromosome DNA in the form of provirus, and it is called as latent infection. The provirus reproduces itself with the replication of the host chromosome, and can bring the infected people into morbidity at any moment if activated by various factors inside and outside the body.

As used herein, "therapy or prevention of viral infection" refers to suppressing the replication and the spread of viruses, preventing the virus self-settling inside the host, and improving or alleviating the symptoms caused by viral infection. The criteria for effective therapy include lower viral load, lower mortality rate, and/or lower morbidity rate, etc.

As used herein, "derivatives" refers to any peptides, homologous to Fusonex, that have the sequence, homologue, analog, or segment of Fusonex, or that have substitute, insertion, and/or deletion of one or more amino acids.

As used herein, "therapeutics" refers to any molecule, compound, or drug conductive to the treatment of viral infection or virus-caused diseases, especially antiviral agents.

As used herein, "synergic action" refers to a joint drug administration that is more effective than the additive action of merely using any of two or more therapeutics to cure or to prevent viral infection. The synergic effect can increase the efficacy of antiviral drugs and avoid or alleviate viral tolerance against any single medicine.

A peptide of the present application is defined as a complex of two or more amino acids linked by peptide bonds. The peptide nomenclature is related to the number of its constitutive amino acids. For example: a dipeptide contains two amino acid residues while a tripeptide contains three, etc. A peptide composed of ten or less amino acids is called an oligopeptide; while a peptide composed of more than ten amino acids is called a polypeptide.

The description for the applications of Fusonex in the treatment of HIV and other viral infection is as follows:

Fusonex is a polypeptide with antiviral activity. The peptides of the present invention include Fusonex (a 36 amino acid peptide derived from gp41), its segments, and/or analogs. These peptides also exist in other envelop viruses. The peptides of the present invention are capable of suppressing the spread of human and other mammal retroviruses, especially HIV.

It is believed that HIV and other viruses replicate themselves ceaselessly 24 hours a day from the moment of infection. Thus, it is necessary to use antiviral agents at different stages of viral infection. The present invention also provides a joint administration of the peptide with different antiviral agents, to inhibit virus-cell fusion and intercellular spread of viruses.

The description of a joint administration of drugs, including Fusonex, for the treatment of HIV infection is as follows:

The acting target of Fusonex is on the glycoprotein gp41 of viral surface. The functional mechanism of Fusonex is to inhibit fusion to prevent free virus granules from infecting other cells, and to prevent the viruses from spreading from infected cells to other cells.

It is believed that Fusonex, when administered jointly with one or more drugs with different targets, may provide additive or synergic effects. The present invention provides a joint administration of drugs, including Fusonex and its derivatives. Joint drug administration can reduce not only the effective dose but also reduce the toxicity of the antiviral drugs. In addition, it can improve the efficacy through a variety of mechanisms for attacking the viruses. Finally, the joint administration of drugs can also prevent or reduce the chances of the development of drug resistance.

The present invention provides a therapeutic method for HIV infection of human and other mammals. This method comprises administering Fusonex or its derivatives in effective dose as well as at least another agent that is preferably a different antiviral agent.

The present invention provides an improved method for the treatment of viral infection (especially HIV infection). The present invention also provides a drug combination for the treatment of HIV infection, the combination has Fusonex or its derivative in effective dose and at least a different antiviral compound. Preferably, Fusonex or its derivative should be used together with retrovirus inhibitors, viral protease inhibitors, cytokines, cytokine inhibitors, or other viral fusion inhibitors. The joint drug administration will be more effective in suppressing viral replication and transmittal.

The methods of the present invention include administration of Fusonex or its derivative alone, and joint drug administration of Fusonex or its derivatives with other antiviral agents. Fusonex and at least one of other agents can be administered simultaneously (used as a mixture or separately), or sequentially (including period therapy). The period therapy administers to the patients an antiviral compound during a certain period and then administering a second antiviral compound during another period. Such administration sequence (namely the period) is repeated to alleviate the toxicity, as well as the drug resistance of the therapy.

The present invention also provides a different period therapy that comprises administering the peptide of the present invention first, and then another antiviral agent, and then the peptide of the present invention again or another viral fusion inhibitor. Consequently, the inhibitor of the present invention or its derivative is administered together with other antiviral agents.

The "joint administration" includes not only using two or more therapeutics together as a mixture therapy, but also using two or more therapeutics separately but simultaneously, for example, via different veins into the same body. The "joint administration" also includes administering the drugs sequentially, namely administering one drug and then the second drug.

The preferred antiviral agents used together with Fusonex can attack the viruses in the following different modes: inhibiting the reverse transcriptase, inhibiting the capping of viral mRNA, inhibiting HIV protease, inhibiting the glycosylation of proteins, inhibiting integrase, and inhibiting viral fusion. Drugs based on those attacking modes above include (but not limited to): antiviral agents, such as the cytokines, including rIFNα, rIFNβ, and rIFNγ, cytokine inhibitors; reverse transcriptase inhibitors, such as AZT, 3TC, ddI, ddC, d4T, Nevirapine, Atevirapine, Delavi Trdine, PMEA, PMPA, Loviride, and other dideoxyribonucleoside or fluorodideoxyribonuceoside; viral protease inhibitors, such as Saquinavir, Ritonavir, Indinavir, Nelfinavir, and VX-478; glycosidase inhibitors, such as SC-48334 and MDL-28574; viral mRNA capping inhibitors such as ribovirin; amphotericin B; ester bond binding molecule castanospermine with anti-HIV activity; hydroxyurea; glycoprotein processing inhibitors; glycosidase inhibitors SC-48334 and MDL-28574; virus absorbent; CD4 receptor blockers; chemokine co-receptor inhibitors; neutralizing antibody; integrase inhibitors and other fusion inhibitors.

A description of the structure of the polypeptide Fusonex is as follows:

Fusonex peptide is a highly-effective fusion inhibitor capable of suppressing HIV infection. Maybe this is because Fusonex can associate with gp41 on viral envelop and interrupt the process of viral fusion. For example, in the course of the viral protein gp41 transformation from natural structure into fusion structure, Fusonex can compete for the binding site on viral gp41 and as a result, destroy the fusion process between the viruses and the cells.

Fusonex, a peptide of the present invention, is derived from the amino acid residues 117-151 of HIV-1 transmembrane protein gp41 and composed of 36 amino acids. Read from the amino terminal to the carboxyl terminal, Fusonex has an amino acid sequence as follows:

```
                                    (SEQ ID NO.: 1)
X-SWETWEREIENYTKQIYKILEESQEQQDRNEKDLLE-Z
```

In addition, the present invention also provides segments of the Fusonex peptide (SEQ ID NO.: 1) that shows an antiviral activity. These truncated Fusonex peptides can contain 4-36 amino acids (namely ranging from tetrapeptide to 36-amino-acid peptide).

"X" is an amino group or -X1-X2, wherein X1 is an imino group, and X2 is a hydrophobic group, including (but not limited to) carbobenzoxy, dansyl, tert-butyloxycarbonyl group, acetyl, and 9-fluorenylmethyloxycarbonyl (FMOC), or a covalent-linked macromolecular vector group, including (but not limited to) lipid-fatty acid chelate,polyethylene glycol and carbohydrate.

Z is a carboxyl group or -Z1-Z2, wherein Z1 is a carbonyl group, and Z2 is an amino group, tert-butyloxycarbonyl group, or a macromolecular vector group, including (but not limited to) lipid-fatty acid chelate, polyethylene glycol and carbohydrate.

In addition to Fusonex and the truncated Fusonex, the inhibitors of the present invention can also be peptides comprising SEQ ID NO.: 1, or peptides comprising SEQ ID NO.: 1 with substitution, insertion, and/or deletion of one or more amino acids. The amino acid insertion can be made up of a single amino acid residue or a residue segment of 2-15 amino acids. One or more insertion can be introduced into Fusonex and its segments, analogs, and/or homologs.

Furthermore, the inhibitors of the present invention include homologs of Fusonex (SEQ ID NO.: 1), analogs of Fusonex homologs, and/or Fusonex segments that show antiviral activity. The inhibitors of the present invention include Fusonex, segments of Fusonex, analogs of Fusonex, and truncated Fusonex homologs. These truncated Fusonex comprise the peptide sequence of Fusonex from which one or more amino acids are deleted, the resulting peptides having a lower limit of 4-6 amino acids. These truncated Fusonex may contain a single adjacent part or more unattached parts of the above mentioned peptide sequence.

According to an embodiment of the present invention, the amino acid substitutes have protective properties. The protective amino acid substitutes comprise of amino acids with similar charges, sizes, and/or hydrophobic characteristics to the amino acids (one or more) they replace in Fusonex (SEQ ID NO.: 1) peptide sequence.

A description of the antiviral agents in joint administration with Fusonex is as follows:

The fusion inhibitors of the present invention can be administered jointly with other therapeutics in order to enhance its antiviral efficacy. According to a preferred embodiment of the present invention, Fusonex is administered with other antiviral agents, including (but not limited to) drugs acting on different targets all through the virus replication process, such as reverse transcriptase inhibitors, viral protease inhibitors and glycosylation inhibitors, etc; antiviral agents acting on different targets all through the virus spreading process; antiviral agents acting on different sites of the same molecule; and antiviral agents capable of preventing or reducing the development of the drug resistance. The working mechanisms as well as the benefits of joint administration should be known to all scientific and technological personnel in the present field.

The inhibitors of the present invention can be administered jointly with retrovirus inhibitors, including (but not limited to) nucleoside derivatives. The nucleoside derivatives are improved derivatives of purine nucleosides and pyrimidine nucleosides. Their acting mechanism is to prevent RNA and DNA from being synthesized. The nucleoside derivatives, in the absence of any 3'substituent that can be bound to other nucleosides, can suppress the synthesis of cDNA catalyzed by reverse transcriptase and thereby terminate the viral DNA replication. This is why they become anti-HIV therapeutic agents. For example, AZT and ddT, both of them can suppress HIV-1 replication in vivo and in vitro, had been approved as remedies for HIV infection and AIDS. However, use of these drugs for treatment can lead to mass propagation of drug-fast HIV strains in addition to many side effects.

The inhibitors of the present invention can be administered jointly with nucleoside derivatives and non-nucleoside derivatives. The nucleoside derivatives include (but not limited to): 2',3'-dideoxyadenosine (ddA); 2',3'-diseoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3'-azide2',3'-dideoxycytidine (AZT). According to an embodiment of the present invention, the nucleoside derivatives are halonucleoside, preferably 2' 3'-dideoxy-2'-fluoronuceotides, including (but not limited to): 2',3'-dideoxy-2'-fluoroadenosine; 2',3'-dideoxy-2'-fluoroinosine; 2',3'-dideoxy-2'-fluorothymidine; 2', 3'-dideoxy-2'-fluorocytidine; and 2',3'-dideoxy-2',3'-didehydro-2'-fluoronuceotides, including (but not limited to): 2',3'-dideoxy-2',3'-didehydro-2'fluorothymidine (Fd4T). More preferably, the nucleoside derivatives are 2',3'-dideoxy-2'-fluoronuceotides wherein the fluorine bond is in the β conformation, including (but not limited to): 2',3'-dideoxy-2'β-fluoroadenosine (F-ddA), 2',3'-dideoxy-2'β-fluoroinosine (F-ddI), 及2',3'-dideoxy-2'β-fluorocytidine (F-ddC). Joint drug administration can reduce the dosage of nucleoside derivatives, and thereby reduce its toxicity as well as drug-resistance of the virus, while maintaining their antiviral activity.

According to a preferred embodiment of the present invention, the combination of antiviral peptides and nucleotide derivatives include Fusonex or its derivatives in effective dose, and AZT, ddC, and/or d4T in effective dose for the treatment of HIV infection. A more preferred drug combination includes (but not limited to): Fusonex or its derivatives and ddT in effective dose; and/or 3TC, Viramune, Rescriptor, Sustiva, Loviride, Nevirapine, and Atevirdine in effective dose.

Fusonex or its derivatives can also be administered jointly with inhibitors of urdine phosphorylating enzyme, including (but not limited to) acyclouridine compounds, including benzylacyclouridine (BAU); benzoxybenzylacyclouridine (BBAU); amethobenzylacyclouridine (AMBAU); amethobenzoxybenzylacyclouridine (AMB-BAU); hydroxymethylbenzylacyclouridine (HMBAU); and hydroxymethylbenzoxybenzylacyclouridine (HMBBAU).

Fusonex or its derivatives can also be administered jointly with cytokines or cytokine inhibitors, including (but not limited to): rIFN$\alpha$, rIFN$\beta$, and rIFN$\gamma$, TNF$\alpha$ inhibitors, MNX-160, human r interferon $\alpha$A, human r interferon $\beta$, and human r interferon $\gamma$. A more preferred joint drug administration includes Fusonex or its derivatives and $\beta$ interferon in effective dose.

Protease inhibitors prevent the virus from maturing mainly during the viral assembly period or after the assembly period (namely during the viral budding). Protease inhibitors show an antiviral activity both in vivo and in vitro. After being administered protease inhibitors, the AIDS patient HIV-level exhibits an exponential decline and their CD4 lymphocytes rise in number (Deeks, et al., 1997, *JAMA* 277:145-53). Joint administration of viral protease inhibitors with fusion inhibitor Fusonex can produce a synergic effect and achieve satisfactory clinical results. The present invention provides a the method for treating HIV infection, which is a joint drug administration using Fusonex or its derivatives in effective dose together with a protease inhibitor in effective dose, the latter including (but not limited to): Indinavir, Invirase, Norvir, Viracept, and Agenerase.

Fusonex or its derivatives can also be used jointly with anti-HIV drugs that disturb 5'-mRNA processing, such as virazole. The acting mechanism of virazole is unknown yet and presumed to be competing with guanine in forming the mRNA capping structure, and/or disturbing the methylation of these molecules. There is likely to be a synergic action between Fusonex and virazole.

In addition, Fusonex or its derivatives can be administered jointly with amphotericin B. Amphotericin B is a polyene antifungal antibiotic that can bind irreversibly with sterol. Amphotericin B and its formate have an inhibiting effect against many lipid envelop viruses including HIV. Amphotericin B has a serious toxicity towards human body while its formate has a much lower toxicity. Thus, Amphotericin B or its formate can be administered jointly with Fusonex or its derivatives, and produce an anti-HIV synergic effect, which allows clinical doctors to use Amphotericin B or its formate in lower doses without losing its antiviral activities.

Fusonex or its derivatives can also be administered jointly with the glycoprotein processing inhibitor castanospermine, which is a vegetable alkaloid capable of inhibiting glycol protein processing. HIV envelope contains two large glycoproteins gp120 and gp41. The glycosylation of proteins plays an important role in the interactions between gp120 and CD4. The progeny virus synthesized in the presence of castanospermine has a weaker infectivity than the parental virus. The joint administration of Fusonex or its derivatives with castanospermine can produce a synergic effect.

The therapeutic effect of the joint administration of Fusonex or its derivatives with the above-mentioned antiviral therapeutics can be evaluated by generally used methods in the present field. For example, the joint effect of Fusonex and AZT can be tested through a variety of in vitro experiments including: inhibiting HIV toxicity against cells, inhibiting the formation of synplasm, inhibiting the activity of reverse transcriptase, or inhibiting viral ability for RNA or protein synthesis, etc.

A description of the dosage formulations, dosage, and administration routes is as follows. Drug combination is described first.

The drug combination of Fusonex or its derivatives with at least one of other therapeutic agents provided by the present invention can be used for the treatment or prevention of human or non-human viral infection. The joint drug administration provided by the present invention can produce an additive/synergic effect.

The preferred drug combination contains Fusonex or its derivatives, and at least one of other antiviral agents, such as reverse transcriptase inhibitors, protease inhibitors, mRNA processing inhibitors, protein glycosylation inhibitors, virus adsorbent, CD4 receptor inhibitors, chemokine co-receptor inhibitors, neutralizing antibody, integrase inhibitors, and other fusion inhibitors, including (but not limited to) nucleoside analogs or chain terminators; chemokine co-receptor inhibitors AMD-3100 (Tremblay, C. L. et al., 2000, *J. AIDS* 1:25(2)99-10).

According to an embodiment of the present invention, therapeutic agents that can be used jointly with Fusonex or its derivatives include (but not limited to): 2-deoxy-D-glucose (2dG1c), deoxynojirimycinacycloguanosine, virazole, rifadin, adamantanamine, rifabutine, ganciclover (DHPG), famciclove, buciclover (DHBG), fluoroiodoaracytosine, iodoxuridine, trifluorothymidine, ara-A, ara-AMP, bromovinyldeoxyuridine, BV-arau, 1-b-D-glycoarabinofuranoside-E-5-[2-bromovinyl]uracil, adamantethylamine, hydroxyurea, phenylacetic heptanedione, diarylamidine, (S)-($\rho$-nitrobenzyl)-6-thioinosine and phosphonoformate. The present invention provides a drug combination of Fusonex or its derivatives with any other above-mentioned compounds.

In addition, the peptides of the present invention can also be used as a preventive measure for individuals who are exposed to HIV but have not been infected by it yet. Examples of such a preventive measure include (but not limited to): the prevention of mother-baby transmittal of the viruses; and the prevention of HIV infection in other situations, such as in medical workers handling HIV-contaminated blood, blood products, and body fluid in a medical accident. In these cases, the peptides of the present invention can be used as a preventive vaccine. With the inoculation of the peptide of the present invention, the host will produce antibodies that can inhibit HIV infection and neutralize HIV viruses.

The present invention provides a preventive vaccination scheme, which comprises: administering to the host the peptide at an effective concentration for eliciting sufficient immune responses to neutralize the HIV, e.g., to develop the ability to inhibit HIV infection of cells. The elicited immune responses can be detected by standard techniques well-known to one of skill in the art. According to an embodiment of the present invention, the peptide used as vaccine is administered by muscle injection.

In order to increase immune responses, the peptide of the present invention can be administered with some proper adjuvants including (but not limited to): mineral gel, such as aluminium hydroxide; surface active substance, such as lysolecithin; Puronic polyhydric alcohol, polyanion; other peptides; oil emulsion agent; and other potential additives for human use, such as Bacillus Calmette-Guérin (BCG) and small coryneform. The routes by which the above-mentioned vaccine is administered include (but not limited to) oral, intradermal, intramuscular, intraperitoneal, intravenous, hypodermal, and mycteric routes.

A description of the dosage of Fusonex is as follows:

In the treatment of acute viral infection in mammals such as human, Fusonex or its derivatives should be administered at an effective dose sufficient to suppress viral replication. This effective dose can be determined by methods generally known to one of skill in the art, including setting parameters such as biological half-life period, bioavailability and toxicity, etc. As an example, Fusonex can be injected continually for 4-52 weeks in a dose of 0.2-10.0 mg/kg a day. A preferred dose is 20 mg~200 mg a day. The most preferred dose is 30 mg-80 mg a day; the duration is about 52 weeks.

The administration interval for Fusonex or its derivatives ranges from about 2 days to ¼ days, most preferably 1-½ days. When in the best dosage, Fusonex or its derivatives can attain a peak concentration of 1 mg/ml-10 mg/ml in blood plasma. The blood concentration of Fusonex can be determined as follows: make up a sterile injection of 20% Fusonex in some proper buffer saline solution and inject it continually, then measure the blood concentration by HPLC.

The effective dose of the therapeutic agents such as the antiviral agents in joint administration with Fusonex or its derivatives is determined on the basis of the recommended dosage of various antiviral agents well-known to one skill in the art. The preferred dosage for joint administration is about 10%-50% lower than the literature-recommended dosage for separate administration. Medical professionals should pay attention to the dosage at which toxic reactions begin to occur. When the functions of marrow, liver and/or kidney are damaged, or serious drug interactions occur, the doctor should know how and when to suspend or terminate the administration and to regulate the dosage to a lower lever. In contrast, if the anticipated clinical therapeutic results are not achieved, the doctor should also know how to enhance the dosage.

An effective therapeutic dosage refers to a dosage at which the drug combination is sufficient to improve the patient's conditions or to prolong his survival period. The toxicity and therapeutic effect of this type of drugs can be determined according to standard pharmacological procedures of cell culture or animal experimentation. For example, the procedures can be determination of the medium lethal dosage ($LD_{50}$, the dosage at which 50% of the experimental colony are killed) and the medium effective dose ($ED_{50}$, the dosage at which 50% of the experimental colony are cured). The ratio of therapeutic ability to toxicity is the therapeutic index and can be represented by $LD_{50}/ED_{50}$. The higher the therapeutic index is, the better the compound is. Statistics obtained in cell and animal experimentation can be used to infer the dosage range for human. The dosage of this kind of compounds lies best within a certain hematic drug concentration range, namely higher than $ED_{50}$ while with no or low toxicity, and then it can be regulated according to the dosage formulation and administration route. Based on these data, the dosage for human use can be determined accurately. The drug concentration in blood plasma can be measured by HPLC.

A description of the dosage formulation and administration routes is as follows:

Patients are administrated directly with the drug combination containing Fusonex or its derivatives, or with the mixture of the drug combination containing Fusonex or its derivatives with some proper carrier or excipient in order to obtain the dosage for treating viral infection, especially HIV infection. The preparation and administration technology for this application is well-known to one of skill in the art.

The antiviral activity of the peptides of the present invention can exhibit a subtype specificity, which means a specific peptide inhibits only a specific virus. The peptides of the present invention are most sensitive to HIV-1, and such an advantage can be utilized in this field of diagnosis reagent. For example, the anti-HIV-1 specificity of this peptide can be used to identify the type of a certain isolated virus strain (HIV-1 or HIV-2). For example, in the presence of the Fusonex peptide, an isolated uninfected CD4+ cell is infected with an unknown virus strain, and then continuation to culture the cell. Afterward, the retrovirus activity of cellular supernatant is tested, and if the activity is totally suppressed, this virus strain should be HIV-1; if the activity is not suppressed or suppressed only a little, the virus strain is not likely HIV-1.

The present invention also includes the use of pharmacologically acceptable carrier to prepare a proper dosage formulation for systematic administration based on the peptides and/or drug combinations of the present invention. With appropriate carrier and formulation, the peptides or the combinations of the present invention, especially the combination prepared as a solution, can be administered by extragastrointestinal routes including (but not limited to) intravenous injection. The peptides or the combinations of the present invention can also be prepared as a solution fit for oral administration by use of a pharmacologically acceptable carrier well-known in the art. Appropriate carriers are necessary for preparing the peptides or combinations into tablets, pills, capsules, liquid, gel, syrups, slurry, suspensions, and other dosage formulations.

The peptides and drug combinations of the present invention can be administered by routes well-known to one of skill in the art, including actinal, rectal, dialysis membrane, or enteric administration; extragastrointestinal administration including intramuscular, hypodermal, intramedullary, introthecal, directly intraventricular, intravenous, intraperitoneal, intranasal, or intraocular injection; percutaneous, local, vaginal administration, etc. The dosage formulations include (but not limited to) tables, pastille, powders, suspensions, suppositories, solution, capsules, frost, plasters, and micro-motors. For convenience, the drug combinations of the present invention can be made up by routine methods into any pharmacologically acceptable formulation using one or more physiologically acceptable carriers. The drug combinations of the present invention can comprise one or more excipient and adjuvant to facilitate the processing of active compounds. The formulation is determined by the administration route. To facilitate the injection, the peptides or combinations of present invention can be prepared as a solution, e.g., a physiological saline solution. In the case of dialysis membrane administration, penetrants that facilitate the preparation penetration of barriers should be used, and these penetrants should be generally known in this field.

The oral dosage formulation of the peptides and drug combinations of the present invention can be ground together with solid excipients into a well-distributed mixture and then processed into granules that are further processed into tablets or the kernel of sugar-coated tablets; if necessary, proper adjuvant can be added to the mixture. Proper excipients and fillers can be sugar, such as lactose, saccharose, mannitol, or sorbicolan; fibrin products, such as cornstarch, wheaten starch, rice starch, potato starch, glutin, tragacanth, methyl cellulose, hydroxypropylmethyl cellulose, sodium carboxymethyl cellulose, and/or polyvinylpyrrolidone. If necessary, disintegrants, such as cross-linked polyvinylpyrrolidone, agar, alginic acid, or its salt-like alginate sodium. Proper coat should be provided to the kernel of sugar-coated tablets. The coat can be made from concentrated sugar solution containing Arabic gum, talcum, polyvinylpyrrolidone, carbopol gel, polyethylene glycol, titanium oxide, cellulose nitrate, and proper organic solvent or solvent combination. Different combinations of coloring matter or edible pigment can be added to the tablets or coat of sugar-coated tablets to discriminate or designate the active compound.

The drug combination for oral administration includes the stuffing-type capsule and the sealed soft capsule made of glutin and a plasticizer such as glycerin or sorbic acid. The stuffing-type capsule contains a filler, such as lactose, an adhesive, such as starch, and/or a lubricant, such as talcum or stearate. In addition, a stabilizer can also be used to stabilize the active components. In the soft capsule, the active compound can be dissolved or suspended in some proper liquid, such as fatty oil, liquid olefin, or liquid-like polyethylene glycol. Besides, a stabilizer can also be added. All the dosage formulations for oral administration should be convenient for patients. In the case of actinal administration, the above mentioned combination can be prepared into the convenient dosage formulations of troche.

In the case of inhalation administration, the peptides or combinations of the present invention can be readily released in the form of aerosil by use of high-pressure package or atomizer, or by use of some proper propellant such as dichlorodifluoromethane, trichlorofluoromethane, dichlorotetrafluoroethane, carbon dioxide or other proper gases. In the case of high-pressure aerosol, the dosage unit can be defined by the quantity of measured release with one valve. The glutin capsule and cartridge used as insufflator or exsufflator can be produced as a mixture containing the peptides and a proper pulverous substrate (such as lactose or starch).

The peptides or combinations of the present invention can be prepared into a dosage formulation for extragastrointestinal administration. For example, they can be prepared into a formulation for injections that include cluster-drug injection or continuous intravenous infusion. The preparation for injection use can be packed in the form of unit dosage. For example, it can be packed into ampoules. Preparations in large dosage can also be packed in the form of unit dosage, such as ampoule or large-dosage container, and added with preservative. The combinations of the present invention can take the form of suspension, solution or emulsion with oil or water as its medium, and can contain some additives, such as a suspending agent, stabilizer, and/or dispersant.

The drug combinations for extragastrointestinal administration can be in a water solution of the active substance, namely the water-dissolved form. The suspension of the active substance can also be produced as a proper oil-like suspension injection. The proper oleophilic solvent or vector includes fatty oil such as gingeli oil, or synthesized fatty acid ester such as ethyl oleate or triglyceride, or liposome. Water-like suspension for injection can contain substance that increases the suspension viscosity, such as sodium carboxymethyl cellulose, sorbic alcohol, and glucosan. The above mentioned suspension can also contain selectively a proper stabilizer or substance that increases the compound solubility in order to prepare a high-concentration solution. The active component of the pulverous injection can be dissolved in some proper solvent, such as sterile water for injection that is in the absence of pyretogen, before administration.

The peptides or combinations of the present invention can also be prepared into rectal dosage formulations such as suppositories or retained enemas. They can be prepared with frequent substrate such as cacao butter or other glyceryl esters.

Apart from the dosage formulations that have been described, the peptides or drug combinations can also be prepared as long-acting dosage formulations that can be administered by hypodermal or intramuscular planting or intramuscular injection. Therefore, the peptides and its derivatives or drug combinations can be prepared with proper polymers, hydrophobes (oil emulsion, for example), ion exchange chromatography, or hardly soluble derivatives, such as hardly soluble salt.

The drug carriers for hydrophobic peptides or combinations of the present invention are a co-dissolved system of organic polymers and aqueous phase that blends with water and contains benzyl alcohol and non-polar surfactant. This co-dissolved system can be a VPD co-dissolved system. VPD is a solution containing 3% (W/V) benzyl alcohol, 8% (W/V) non-polar surfactant multiethoxyaether and 65% (W/V) polyethylene glycol 300 in absolute alcohol, while a VPD co-dissolved system (VPD: 5W) is prepared with VPD diluted in water by 1:1 and 5% glucose. This kind of co-dissolved system can dissolve hydrophobes better while it will produce low toxicity in systemic administration. As long as its solubility and toxicity are not changed, the proportions of the co-dissolved system can be altered greatly. In addition, the components of the co-dissolved carrier can also be changed. For example, other non-polar surfactant with low toxicity can be used to substitute for multi-ethoxyaether; the proportion of polyethylene glycol can also be changed; other biologically-blending polymers, such as polyvinylpyrrolidone, can be used to substitute for polyethylene; other sugar or polyose can be used to substitute for glucose.

The drug combinations can also include proper carrier-like excipients in solid or gel phase. These carriers or excipients include (but not limited to) calcium carbonate, calcium phosphate, various sugar, starch, cellulose derivatives, gelatin, or polymers, such as polyethylene glycol. The drug combinations of the present invention also include the combination of active components in effective dose used to obtain the therapeutic purpose. The method of determining effective dose is well-known to one of skill in the art.

A description for the uses of peptides of the present invention is as follows:

The Fusonex peptide (SEQ ID NO.: 1) shows an effective antiviral activity. As a result, the peptide and its derivatives can be used as human and non-human retrovirus inhibitors, especially, HIV inhibitors, and thus preventing the virus from spreading to uninfected cells.

The peptides of the present invention can be used to suppress the spread of human retroviruses, including (but not limited to) HIV-1 and HIV-2 strains and human T-lymphocytes (HTLV-I and HTLV-II). The peptides of the present invention can also be used to suppress the spread of non-human retroviruses, including (but not limited to) Boving leucosis virus, feline sarcoma virus, leucovirus, simian immunodeficiency, leucosis virus, leucovirus, and ovine progressive pneumonia virus.

The peptides of the present invention are also likely to suppress the spread of other retroviruses and/or non-retroviruses, including (but not limited to) human respiratory syncytial virus, distemper virus, Newcastle disease virus, human parainfluenza virus and influenza virus.

Furthermore, the present invention also provides the use of the peptides in joint drug administration for the treatment of diseases caused by the above-mentioned retroviruses and non-retroviruses.

A description for the uses of joint administration for suppressing HIV is as follows:

The present invention provides joint administrations of Fusonex and other therapeutic agents. The joint drug administration can prevent synplasm formation and HIV replication, and thus suppressing the reproduction of HIV in the patients. The joint administrations of the present invention can also be used to alleviate or cure the diseases associated with HIV infection. For example, antiviral peptide Fusonex or its derivatives can be administered jointly with antifunal agents, antibiotics, or other antiviral agents to suppress HBV, EBV, CMV infection and other accidental infection (including TB).

The best use for Fusonex or its derivatives is to suppress HIV infection. The effective dose for joint administration can be based on the methods as follows. For example, to prepare the drug in a proper carrier and to administer it by any proper routes, including (but not limited to): injection (such as intravenous, intraperitoneal, intramuscular, and hypodermal injection, etc.); epithelium or mucosa absorption, such as actinal mucosa, rectal, vaginal epithelium, pharynx nasalis mucosa, enteric mucosa, etc; per os; transdermal or other pharmacologically feasible administration routes.

Compared with existing drugs in the art, the peptides of the present invention has the following advantages: a remarkably improved efficacy for suppressing HIV membrane fusion, a better stability and a higher valence; while the efficacy is improved, the dosage can be reduced and therefore the side effects are reduced.

EXAMPLES

Example 1

Production and Purification of Fusonex

Fusonex was synthesized on the 431A-typed biosystem polypeptide synthesizer. The Fast-Moc chemical method was used in this synthesis, and standard solid-phase synthesizing technique was used with amino acids protected with 9-fluorenylmethyloxycarbonyl (FMOC). The reagents include TFA, water, 5% anisyl sulfide, 2.5% ethylene disulfhydrate, and 0.8M crystalline phenylphenol.

In order to prolong the biological half-life of Fusonex, its amino terminal was acetylated, and carboxyl terminal was amidated. The peptide was automatically dissociated from the resin on the apparatus, and the side chain bulky groups were automatically removed. Dissociated from the resin, the crude Fusonex peptide was precipitated for 20 minutes in cold ether at four-fold volume. After the centrifugation, the peptide was washed two times in cold ether and then dried for 24 hours.

The crude Fusonex peptide was purified by HPLC. On the C18 column (15 µm global filler), linear elution was carried out in water/acetonitrile containing 0.1% TFA. The purity of the purified Fusonex peptide, which was measured by analytical HPLC, was higher than 95%. At last, Fusonex is verified by amino acid sequencing and electron jet mass-spectra. The molecular weight of purified Fusonex was 4641.24D.

Example 2

An Elution Experiment of Fusonex

The method used in Fusonex elution experiment is as follows:

On Superdex 75 chromatography column, the excess Fusonex and the complex of Fusonex and gp41 N-peptide (35-70) was eluted. The eluent was phosphate buffer. The total collection volume for the curve was 30 ml. According to the results, an elution profile (FIG. 2) was drawn, which has shown that the elution peak of the complex of Fusonex and gp41 N-peptide (35-70) was at the position of 13.2 ml, and that of Fusonex itself was at the position of 17.3 ml.

Example 3

Determination of the Structure of Fusonex Complexed with gp41 N-Peptide

Circular dichroism spectra were used to determine the structure of Fusonex complexed with gp41 N-peptide. First, the sample was diluted to 25 µM, pH 7.4 in 0.1 M NaCl/20 mM kalium phosphate, and then the secondary structure of Fusonex complexed with gp41 N-peptide was determined by CD spectra. The analysis was carried out on Aviv 62A DS circular dichroism spectrum apparatus. The peptide solution containing Fusonex and gp41 N-peptide (35-70) was measured in a wavelength range of 200-260 nm.

The conditions for the circular dichroism spectra were: 20° C., the breath of circularly polarized light was 1.5 nm, and the step was 0.5 nm, the time constant was 2.0 seconds, and the length of light cell was 10 mm. Three-level polynomial was used for the correction with the blank data. The temperature of sample was maintained with thermoelectric holder and its error range was within 1° C.

The results were shown in the circular dichroism (CD) spectra (FIG. 3). According to FIG. 3, it has been shown that the complex of Fusonex and gp41 N-peptide (35-70) had a secondary structure of 100% α-helices. Degree (θ) was used as the unit of the ellipticity of the spectrum y-axis, its ellipticity θ was about −40,000/deg cm$^2$ dmol$^{-1}$ (FIG. 3) at 222 nm.

Example 4

Testing the Stability of Fusonex and T-20

This experiment determined the stability of a polypeptide by measuring its melting curve at different temperatures. The experiment was carried out on Aviv 62A DS circular dichroism spectrum apparatus. The temperature range for heating peptide solution was from 20° C. to 95° C.

This experiment tested the stability of a polypeptide based on to its melting curve at different temperatures. The 50% melting temperature for Fusonex complexed with gp41 N-peptide (the curve on the right side, represented by solid circles) is 70° C., while the 50% melting temperature for T-20 complexed with gp41 N-peptide (the curve on the left side, represented by open circles) is 51° C. When other conditions were the same, Fusonex complex needs a higher temperature to melt.

The results were shown in the melting curve (FIG. 4) of Fusonex complex and T-20 complex. According to FIG. 4, it has been shown that the stability of Fusonex was higher than that of T-20.

Example 5

The Inhibitory Activity of Fusonex Against HIV-1 Infection

In this implementing example, it has been shown in the cell-cell fusion assay that Fusonex can block viral infection very effectively. In the fusion assay under the same conditions, the $IC_{50}$ of Fusonex was 1.2±0.2 nM, while the $IC_{50}$ of T-20 was 23±6 nM. The 50% inhibiting concentration ($IC_{50}$) of Fusonex was about 20 times lower than that of T-20. It has be shown by its high valence that Fusonex was more effective in preventing HIV viruses from fusing with human cells, as well as inhibiting HIV-induced intracellular fusion, thus blocking the virus invasion into uninfected cells.

The detailed description of the assay is as follows:

The antiviral activity of Fusonex can be determined by in vitro testing. In the present invention, a luciferase experiment was used to quantificationally test the ability of Fusonex to inhibit the formation of synplasm induced by HIV-1 $gp160_{HXB}$.

The specific experiment methods are as follows: The T7 promoter was inserted into the pSP64 upstream sequence of the cloning site to assemble a luciferase reporter gene plasmid—Pst7luc. The internal ribozyme entry site (IRES) of encephalomyocarditis virus (CMCV) was linked with the 5'-terminal of luciferase gene as well as the downstream area of T7 promoter. CD4 gene, T7 polymerase gene, and HIV-1 $gp160_{HXB}$ gene were subcloned into the mammalian expression plasmid—PMT3.

In a 10 cm culture dish, the 293T cells were transferred by Calcium Phosphate Method. Equal quantities of $gp160_{HXB}$ gene and T7 polymerase gene were used to transfect the effector cells, and pSP64 and CD4 gene were used to transfect the target cells. The PMT3 plasmid in the absence of $gp160_{HXB}$ or CD4 gene was set as a negative control.

The cells with non-serous DMEM were rinsed, after the DNA precipitate was added. The cells were cultured for 30-40 minutes at 37° C. in 9 ml/dish non-serous DMEM. Afterwards, the cells were stirred up and down gently in the dish by pumping with a transfer pipette, and then the cells precipitated after centrifugation were collected. Cells in each dish were resuspended in 3 ml~4 ml DMEM containing 10% FBS, and then the effector cells were mixed with target cells (45 µl each) in 96-well culture plate so as to achieve a well-distributed state.

First, Fusonex or T-20 was dissolved in DMSO, and then diluted by 20-fold. The solution as a stock solution was put to serial dilution in culture medium before use. In each well, 10 µl culture medium or PBS was added, or Fusonex or T-20 diluent was added at concentrations augmenting continuously from zero. The mixture of target cells, effector cells, and the fusion inhibitor were stirred, and then cultured at 37° C. for 8 hours. Before analyzing the luciferase gene, first the culture media were blotted in wells and then the cells were dissolved in 60 µl cytolytic buffer at a 1:1 concentration. 40 µl lysate was transferred to each well of the black 96-well culture plate and then 100 µl fluorecein and coenzyme A were added. Three samples for each concentration point were repeated. Two minutes after adding luciferase substrate to the black 96-well culture plate, measure the chemical fluorescence intensity with Spex fluorolog-3 fluorimeter, the emission wavelength being 552 nm and slit breadth being 7 mm. The average and standard deviation were calculated from the three data of each concentration point.

The inhibition data in the experiment was fitted with the simple affinity balance formula (% luciferase activity=100/$(1+(C/IC_{50}))$) and then reckoned up the $IC_{50}$ value. The results were shown in the inhibition profiles of Fusonex and T-20 against viral fusion (FIG. 5). FIG. 5 indicated that the 50% inhibition concentration ($IC_{50}$) of Fusonex (circles) was about 1/20 of that of T-20 (squares). The $IC_{50}$ value was 1.2±0.2 nM for Fusonex, while it is 23±6 nM for T-20. In other words, the valence for Fusonex fusion inhibition was 20 times higher than that of T-20.

In conclusion, Fusonex is a compound capped at both terminals and composed of 36 amino acids in a specific sequence. This inhibitor and its combination have a strong inhibitory activity against HIV infection, as well as with better stability and higher valence. Therefore, it can improve therapeutic efficacy while requires a lower dose, which could reduce the side effects.

---

We claim:

1. A method of inhibiting fusion of HIV with a biological membrane comprising administering an effective amount of a composition comprising a fusion inhibitor that comprises an amino acid sequence as follows:

X-SWETWEREIENYKQIYKI-
LEESQEQQDRNEKDLLE-Z                (SEQ ID NO: 1)

wherein

X is either an amino group or -X1-X2, wherein X1 is an imino group, and X2 is selected from a group consisting of an acetyl group, a hydrophobic group, and a macromolecular carrier group; and Z is either a carboxyl group or -Z1-Z2, wherein Z1 is a carbonyl group and Z2 is selected from a group consisting of an amino group, a tert-butyloxycarbonyl group, a hydrophobic group, and a macromolecular carrier group.

2. The method of claim 1 wherein the hydrophobic group is selected from the group consisting of a carbobenzoxy, a dansyl, a tert-butyloxycarbonyl, and a 9-fluorenylmethyloxycarbonyl; and wherein the macromolecular carrier group is selected from the group consisting of a lipid-fatty acid chelate, a polyethylene glycol, and a carbohydrate.

3. The method of claim 1 wherein X2 is an acetyl group and Z2 is an amino group.

4. The method of claim 1, wherein the composition also comprises at least one component selected from the group consisting of reverse transcriptase inhibitors, virus protease inhibitors, glycosidase inhibitors, viral mRNA capping inhibitors, amphotericin B, ester-bond binding molecules with anti-HIV activity, hydroxyurea, α-interferon, β-interferon, and γ-interferon.

5. The method of claim 4 wherein the reverse transcriptase inhibitor is at least one component selected from the group consisting of AZT, ddI, ddC, ddA, d4T, 3TC, Nevirapine, Atevirapine, Delavirdine, PMEA, PMPA, and Loviride; wherein the virus protease inhibitor is at least one component selected from the group consisting of Aquinarir, Ritonavir, Indinavir, Nelfinavir, and VX-478; wherein the glycosidase inhibitor is SC-48334 or MDL-28574 or both; wherein the viral mRNA capping inhibitor is Ribovirin.

6. The method of claim 1, wherein said composition is administered in a manner selected from the group consisting of intramuscular, intravenously, subcutaneously, orally, rectally, and percutaneously.

7. The method of claim 2, wherein said composition is administered in a manner selected from the group consisting of intramuscular, intravenously, subcutaneously, orally, rectally, and percutaneously.

8. The method of claim 3, wherein said composition is administered in a manner selected from the group consisting of intramuscular, intravenously, subcutaneously, orally, rectally, and percutaneously.

9. The method of claim 3, wherein said composition is administered in a manner selected from the group consisting of intramuscular, intravenously, subcutaneously, orally, rectally, and percutaneously.

10. The method of claim 5, wherein said composition is administered in a manner selected from the group consisting of intramuscular, intravenously, subcutaneously, orally, rectally, and percutaneously.

* * * * *

UNITED STATES PATENT AND TRADEMARK OFFICE
CERTIFICATE OF CORRECTION

PATENT NO. : 7,335,727 B2
APPLICATION NO. : 11/265892
DATED : February 26, 2008
INVENTOR(S) : Genfa Zhou and Wangni Tian It is certified that error appears in the above-identified patent and that said Letters Patent is hereby corrected as shown below:

Column 1,
Line 56, "genotype" should read --genotypes--.

Column 5,
Lines 22-23, "XYTSLIHSLIEESQNQQEKNEQELLELK-WASLWNWF-Z." should read --XYTSLIHSLIEESQNQQEKNEQELLELDKWASLWNWF-Z.--.

Column 7,
Line 36, "formulation;" should read --formulation.--.

Column 8,
Line 2, "inventional" should read --invention--.

Column 11,
Line 16, "as latent" should read --a latent--.

Column 14,
Line 49, "fluoronuceotides" should read --fluoronucleotides--.
Line 53, "fluoronuceotides" should read --fluoronucleotides--.
Line 56, "fluoronuceotides" should read --fluoronucleotides--.

Column 15,
Line 7, "urdine" should read --uridine--.
Line 31, "a the method" should read --a method--.

Column 17,
Line 28, "one skill in the art" should read --one skilled in the art--
Line 36, "lower lever" should read --lower level--.
Line 43, "this type of drugs" should read --these types of drugs--.
Line 54, "range for human." should read --range for humans.--.
Line 55, "compounds" should read --compound--.

Column 18,
Line 55, "preparation penetration of barriers" should read --preparation of penetration of barriers--.

Column 19,
Line 25, "aerosil" should read --aerosol--.

Column 20,
Line 31, "surfactant with low" should read --surfactants with low--.

UNITED STATES PATENT AND TRADEMARK OFFICE
CERTIFICATE OF CORRECTION

PATENT NO. : 7,335,727 B2
APPLICATION NO. : 11/265892
DATED : February 26, 2008
INVENTOR(S) : Genfa Zhou and Wangni Tian It is certified that error appears in the above-identified patent and that said Letters Patent is hereby corrected as shown below:

Column 21,
Line 15, "with antifunal" should read --with antifungal--.
Line 31, "invention has the" should read --invention have the--.
Line 43, "431A-typed" should read --431A-type--.

Column 22,
Line 31, "the breath" should read --the breadth--.
Lines 55-56, "based on to its melting" should read --based on its melting--.

Column 23,
Line 12, "It has be shown" should read --It has been shown--.

Column 25,
Line 21, "X-SWETWEREIENYKQIYKI" should read
--X-SWETWEREIENYTKQIYKI--.

Signed and Sealed this

Eleventh Day of November, 2008

JON W. DUDAS
*Director of the United States Patent and Trademark Office*

SEQUENCE LISTING

```
<160> NUMBER OF SEQ ID NOS: 2

<210> SEQ ID NO 1
<211> LENGTH: 36
<212> TYPE: PRT
<213> ORGANISM: Artificial Sequence
<220> FEATURE:
<223> OTHER INFORMATION: a peptide derived from HIV trans-membrane
      glycoprotein gp41

<400> SEQUENCE: 1

Ser Trp Glu Thr Trp Glu Arg Glu Ile Glu Asn Tyr Thr Lys Gln Ile
1               5                   10                  15

Tyr Lys Ile Leu Glu Glu Ser Gln Glu Gln Gln Asp Arg Asn Glu Lys
            20                  25                  30

Asp Leu Leu Glu
        35

<210> SEQ ID NO 2
<211> LENGTH: 35
```

```
-continued
<212> TYPE: PRT
<213> ORGANISM: Human immunodeficiency virus type 1

<400> SEQUENCE: 2

Trp Ile Glu Trp Glu Arg Glu Ile Ser Asn Tyr Thr Asn Gln Ile Tyr
1               5                   10                  15

Glu Ile Leu Thr Glu Ser Gln Asn Gln Gln Asp Arg Asn Glu Lys Asp
            20                  25                  30

Leu Leu Glu
        35
```